US010888996B2

(12) United States Patent
Tabandeh et al.

(10) Patent No.: US 10,888,996 B2
(45) Date of Patent: Jan. 12, 2021

(54) ROBOTIC SYSTEM WITH INTUITIVE MOTION CONTROL

(71) Applicant: THINK SURGICAL, INC., Fremont, CA (US)

(72) Inventors: Saleh Tabandeh, Fremont, CA (US); Timothy Pack, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 299 days.

(21) Appl. No.: 15/563,286

(22) PCT Filed: Apr. 4, 2016

(86) PCT No.: PCT/US2016/025917
§ 371 (c)(1),
(2) Date: Sep. 29, 2017

(87) PCT Pub. No.: WO2016/161444
PCT Pub. Date: Oct. 6, 2016

(65) Prior Publication Data
US 2018/0065252 A1 Mar. 8, 2018

Related U.S. Application Data

(60) Provisional application No. 62/142,624, filed on Apr. 3, 2015.

(51) Int. Cl.
*B25J 9/16* (2006.01)
*A61B 34/30* (2016.01)
(Continued)

(52) U.S. Cl.
CPC ............ *B25J 9/1664* (2013.01); *A61B 34/30* (2016.02); *B25J 9/1602* (2013.01); *B25J 9/1694* (2013.01);
(Continued)

(58) Field of Classification Search
None
See application file for complete search history.

(56) References Cited

U.S. PATENT DOCUMENTS 6,212,443 B1 * 4/2001 Nagata ................. G05B 19/423
700/245
8,388,605 B2 * 3/2013 Umemoto .............. A61B 34/71
606/1
(Continued)

OTHER PUBLICATIONS

International Search Report dated Jul. 25, 2016 for International Application No. PCT/US2016/025917, filed Apr. 4, 2016.

*Primary Examiner* — Bhavesh V Amin
(74) *Attorney, Agent, or Firm* — Blue Filament Law PLLC

(57) ABSTRACT

A robotic system includes a base with a manipulator is attached to the base. At least one sensor is associated with the manipulator. The at least one sensor detects a trajectory of an external disturbance on the manipulator or an external cue from a user. A controller is provided that converts the trajectory detected by the at least one sensor to an input signal or the external cue detected by the at least one sensor to an input signal. A drive system receives the input signal, and in response to the input signal powers the base or to power the base in a trajectory corresponding to the external cue. A method for intuitive motion control of the robotic system is also provided.

19 Claims, 4 Drawing Sheets

(51) Int. Cl.
 *G05B 19/423* (2006.01)
 *A61B 17/00* (2006.01)
 *A61B 90/00* (2016.01)

(52) U.S. Cl.
 CPC .. *G05B 19/423* (2013.01); *A61B 2017/00203* (2013.01); *A61B 2017/00207* (2013.01); *A61B 2090/064* (2016.02); *A61B 2090/066* (2016.02)

(56) References Cited

U.S. PATENT DOCUMENTS

| | | | |
|---|---|---|---|
| 8,494,677 B2 * | 7/2013 | Mizutani | G05B 19/423 700/245 |
| 8,774,969 B2 * | 7/2014 | Schreiber | B25J 9/1656 700/250 |
| 9,259,281 B2 * | 2/2016 | Griffiths | A61B 34/70 |
| 10,324,425 B2 * | 6/2019 | Takahashi | G05B 9/02 |
| 2004/0181312 A1 * | 9/2004 | Miura | B25J 13/085 700/258 |
| 2005/0222714 A1 * | 10/2005 | Nihei | G05B 19/423 700/264 |
| 2005/0244260 A1 * | 11/2005 | Deplano | B25J 19/005 414/730 |
| 2007/0142823 A1 * | 6/2007 | Prisco | B25J 9/1638 606/1 |
| 2007/0163816 A1 | 7/2007 | Schena et al. | |
| 2009/0228019 A1 | 9/2009 | Gross et al. | |
| 2010/0145520 A1 * | 6/2010 | Gerio | B25J 13/06 700/264 |
| 2012/0029663 A1 | 2/2012 | Danko | |
| 2012/0226448 A1 * | 9/2012 | Mutsaerts | B25J 13/02 702/41 |
| 2012/0239193 A1 * | 9/2012 | Mizutani | G05B 19/423 700/250 |
| 2013/0268118 A1 * | 10/2013 | Grinstead | B25J 19/023 700/259 |
| 2013/0268120 A1 * | 10/2013 | Grygorowicz | B25J 1/02 700/264 |
| 2014/0052153 A1 * | 2/2014 | Griffiths | A61B 34/70 606/130 |
| 2014/0222023 A1 | 8/2014 | Kim et al. | |
| 2015/0217445 A1 * | 8/2015 | Hietmann | B25J 9/0081 700/264 |
| 2015/0224639 A1 * | 8/2015 | Dockter | B25J 3/04 700/264 |
| 2017/0028553 A1 * | 2/2017 | Tsuda | B25J 13/084 |
| 2017/0354468 A1 | 12/2017 | Johnson et al. | |
| 2018/0065252 A1 * | 3/2018 | Tabandeh | A61B 34/30 |
| 2018/0107174 A1 * | 4/2018 | Takahashi | G05B 9/02 |

* cited by examiner

US 10,888,996 B2

ROBOTIC SYSTEM WITH INTUITIVE MOTION CONTROL

This application claims priority benefit of U.S. Provisional Application Ser. No. 62/142,624 filed 3 Apr. 2015; the contents of which are hereby incorporated by reference.

FIELD OF THE INVENTION

The present invention generally relates to robotic systems, and more specifically to a robotic system with intuitive motion control.

BACKGROUND OF THE INVENTION

Robotic systems have been developed to aid in a variety of different applications ranging from the industrial, medical, and military fields. Robotic systems have unique characteristics to perform different tasks depending on the application. The size, weight, geometry, construction, controls, programs and functionality are all characteristics that need to be considered when designing a robot for any given application.

The maneuverability of large and heavy robotic systems is of particular concern. A robotic system may need to be mobile in one aspect to reach a designated working area. Once in the working area, the robot needs to remain stationary such that the end-effector or working potion of the robot can perform a task. For example, the ROBODOC® Surgical System (Think Surgical, Inc., Fremont, Calif.) is a computer-assisted surgical system that aids surgeons in preparing the femoral canal in total hip arthroplasty. The ROBODOC® system is manually steered to the surgical site and a braking mechanism then locks the system in place to allow the robotics arm to accurately mill the cavity of the femoral canal to receive an implant. However, manually steering the robot is a difficult process due to the sheer size and weight of the system. Additionally, the robotics surgical system needs to be accurately positioned and oriented such that the robotics arm is in an operable workspace to accurately and safely perform the procedure. The manual steering of the robotics surgical system may require multiple attempts to achieve the correct position and orientation in the operable workspace.

Thus there is a need in the art for a more intuitive steering mechanism to more easily move and accurately position a robotics system to perform a specified task.

SUMMARY OF THE INVENTION

A robotics system includes a base with a manipulator is attached to the base. At least one sensor is associated with the manipulator. The at least one sensor detects a trajectory of an external disturbance on the manipulator. A controller is provided that converts the trajectory detected by the at least one sensor to an input signal. A drive system receives the input signal, and in response to the input signal powers the base.

A robotics system includes a base with a manipulator is attached to the base. At least one sensor detects an external cue from a user. A controller converts the external cue detected by the at least one sensor to an input signal. A drive system that receives the input signal to power the base in a trajectory corresponding to the external cue.

A method for intuitive motion control of a robotics system includes an external disturbance being applied to a manipulator of the robotics system. A trajectory of the external disturbance is detected. A drive system is powered to move the robotics system in the trajectory of the external disturbance.

BRIEF DESCRIPTION OF THE DRAWINGS

The present invention is further detailed with respect to the following drawings that are intended to show certain aspects of the present invention, but should not be construed as a limit on the practice of the present invention

DETAILED DESCRIPTION OF THE INVENTION

The present invention has utility as a robotics system with intuitive motion control to provide an accurate and efficient method to position and orient a robotics base. The following description of various embodiments of the invention is not intended to limit the invention to these specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As reference will be made to the ROBODOC™ Surgical System, it should be appreciated that any autonomous, semi-autonomous, or haptic robotics system either for medical or industrial applications may benefit from the system and methods disclosed herein.

As used herein the term 'trajectory' refers to one of a direction, rotation, velocity, acceleration, and any combination thereof.

Embodiments of the present invention describe a system and method to intuitively control the positioning and orientation of a robotics base.

Figure 1:
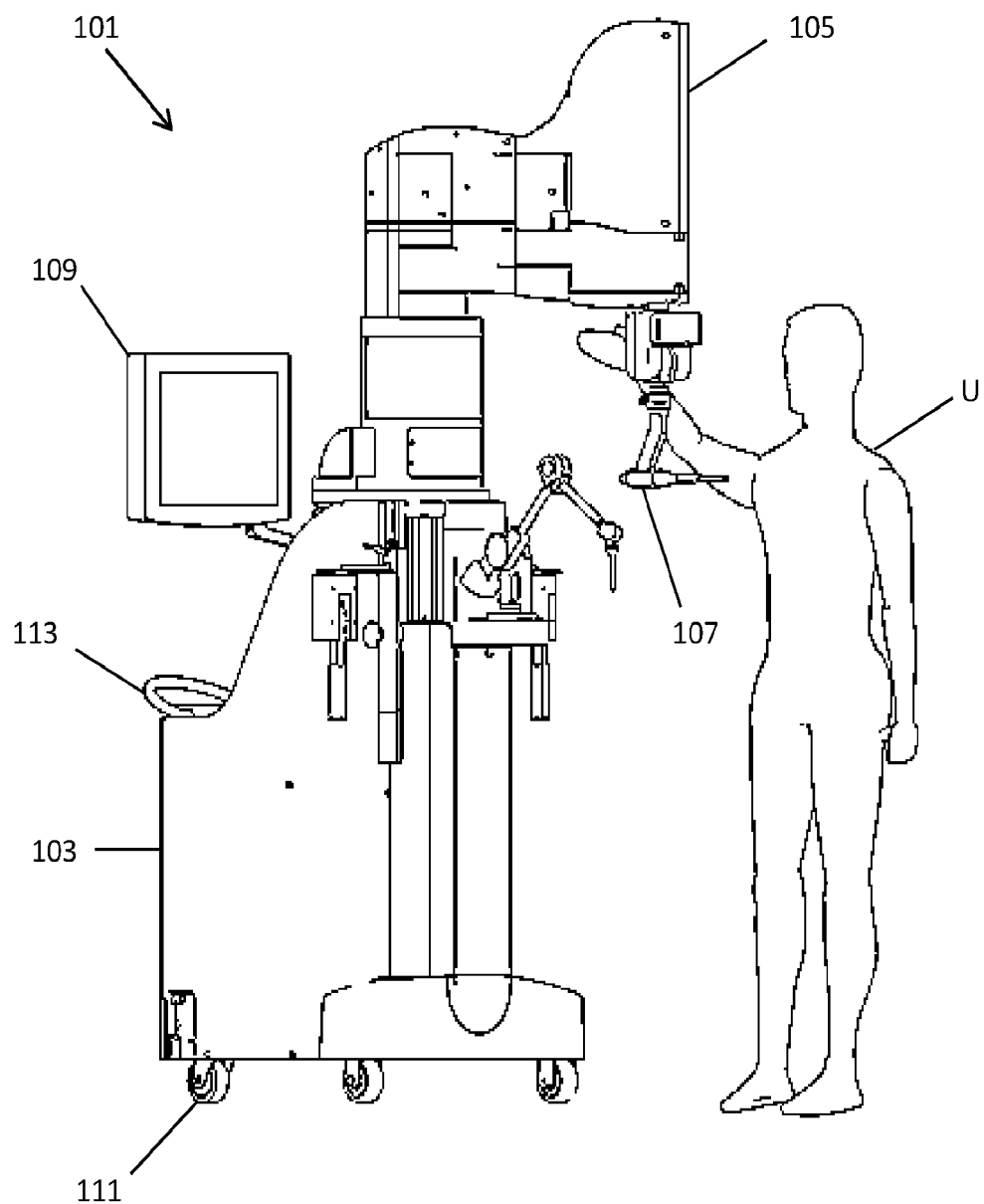
FIG. 1 is a perspective view of a robotics system with intuitive motion control in accordance with embodiments of the invention.

Referring now to the figures, FIG. 1 depicts a robotics system 101 in accordance with an embodiment of the invention. The robotics system 101 may include a base 103, a manipulator 105, a display monitor 109, wheels 111 and a steering handle 113. Normally, a user, U maneuvers the robotics system 101 by grasping the steering handle 113 and guides the base 103 to a desired position and orientation such that the manipulator 105 is in an operable workspace. It is appreciated that other embodiments of the present invention allow the user U to maneuver the base 103 by applying an external disturbance on the manipulator 105.

Figure 2:
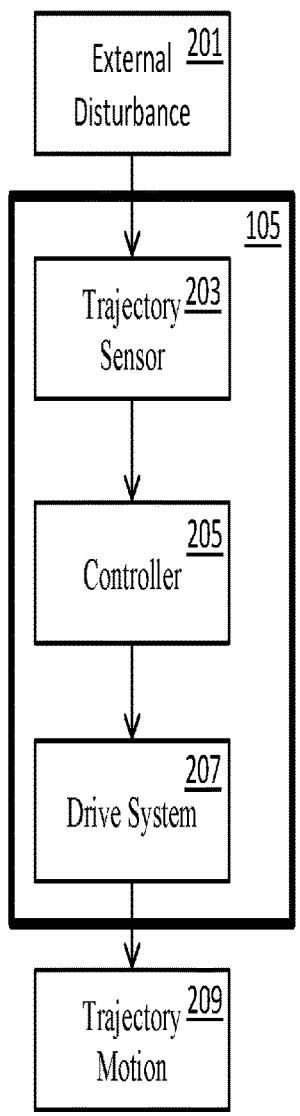
FIG. 2 is a flowchart of a method to control the trajectory of a robotics base in accordance with embodiments of the invention.

FIG. 2 is a functional block diagram of the manipulator 105, and includes at least one sensor (Block 203) for detecting the trajectory of the external disturbance (Block 201) applied on the manipulator 105 by the user U. In specific inventive embodiments, the at least one sensor may be at least one of a linear encoder, rotary encoder, transducer, Hall effect sensor, force sensor, a torque sensor, or combinations thereof. The trajectory corresponds to a direction, rotation, velocity, or acceleration the user U desires the base 103 to move. The detected trajectory from the trajectory sensor 203 is sent to a controller (Block 205), and the controller 205 generates an input signal for a drive system (Block 207) to power the base 103 in the desired trajectory (Block 209). Therefore, the robotics system 101 is configured to provide intuitive motion control to position and orient the base 103 accurately and efficiently in response to a user initiated touch or disturbance. It should be appreciated that the controller (Block 205) and the drive system (Block 207) may be located in the base 103 of the robotics system 101.

Figure 5:
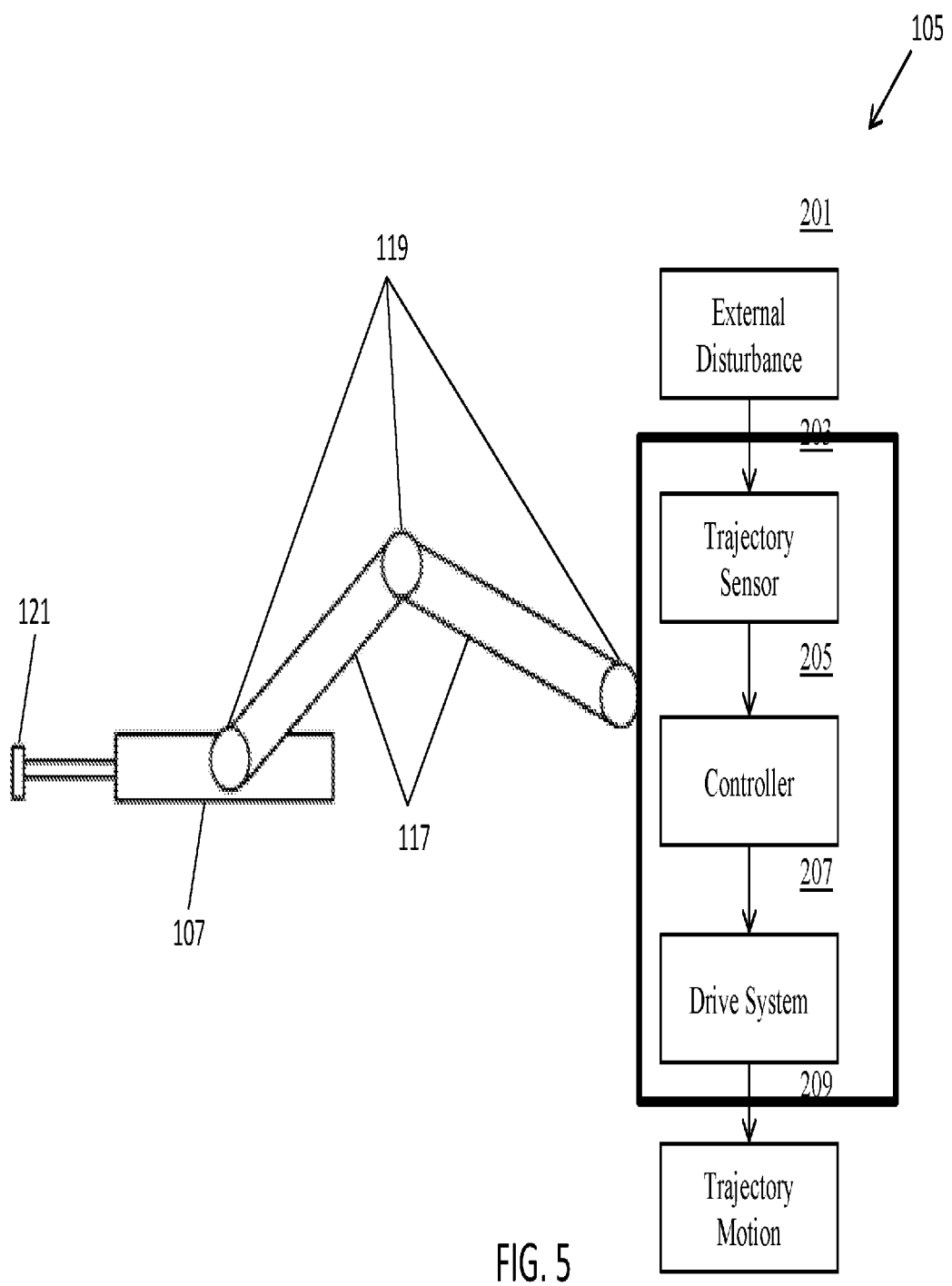
FIG. 5 is a detail view of a manipulator and end effector in accordance with embodiments of the invention.

In another specific inventive embodiment, the manipulator 105, as shown in detail in FIG. 5, may include various links 117 and joints 119 with an end-effector 107 at the most distal link. The links 117 may be of any size and geometric shape that are connected, either in series or parallel, by joints 119. The joints 119 may be revolute, linear, or spherical. The manipulator 105 generally has at least one joint to provide one degree of freedom, but preferably more to conduct complex tasks. The revolute, linear, or spherical joints 119 may include rotary, linear, or spherical encoders respectively such that the position and orientation of each joint 119 may be determined by the robotics system 101. The end-effector 107 may include a tool 121 to perform a specific task. For example, in total hip arthroplasty, the end-effector 107 may have a tool 121 that is a cutter or burr to mill the femoral cavity to receive an implant.

In a specific inventive embodiment, a force and/or torque sensor may also be incorporated with any of the links 117, joints 119, or end-effector 107 to measure an applied force and torque. The force and/or torque sensor is capable of detecting a magnitude and at least one direction of the force applied to at least a portion of the manipulator 105. The force and/or torque sensor in certain inventive embodiments is capable of detecting the force in three directions (x,y,z) and three rotations (pitch, yaw, roll) known as a 6-axis force/torque sensor or a subset thereof. Corresponding resultant forces in any direction may be calculated from the force/torque sensor. In an embodiment, the force and/or torque sensor may be incorporated between a most distal link and end-effector 107 of the manipulator 105. In a specific inventive embodiment, the force and/or torque sensor may be incorporated between the base 103 and the most proximal link of the manipulator 105. It should be appreciated that multiple force and/or torque sensors may be incorporated at various links and/or joints of the manipulator 105.

In certain inventive embodiments of the robotics system 101, the sensor(s) such as the encoder(s) and/or force/torque sensor(s) are electrically or wirelessly connected to the controller 205. The controller 205 may be an open loop or closed loop controller capable of reading the sensor data. The controller 205 may include a processor with memory to execute a set of instructions. In an embodiment a set of programmable manipulator instructions may execute a surgical procedure based on a surgical plan. The controller 205 may further include an analog to digital converter, a rectifier, a comparator, as well as any other components well known in the art to read and convert the sensor data to trajectory output signals. The trajectory output signals are sent as input signals to at least one drive system 207. The drive system(s) 207 may include one or more motors or actuators that are controlled electrically or pneumatically. The input signals are generated such that the drive system powers a transportation mechanism on the bottom of the base 103 (e.g., wheels, inflatable bladder, continuous track) in the trajectory detected by the sensor 203 corresponding to the trajectory of the external disturbance applied to the manipulator 105.

In certain inventive embodiments, the user U may apply an external disturbance 201 to any portion of the manipulator 105. For example, when a force/torque sensor is incorporated between the most distal link and end-effector 107 of the manipulator 105, the user U may create an external disturbance by grasping, pushing, pulling, or rotating the end-effector 107. The force/torque sensor detects the direction, rotation and/or magnitude of the external disturbance 201 such that the base moves accordingly. If the force/torque sensor is located between the base 103 and the most proximal link of the manipulator 105, the user U may apply an external disturbance 201 to any portion of the manipulator 105 to cause the base 103 to move accordingly. It should be appreciated that one or more force/torque sensors may be positioned at various locations on the manipulator 105 such that the user U may apply an external disturbance 201 at different locations on the manipulator 105.

Figure 3:
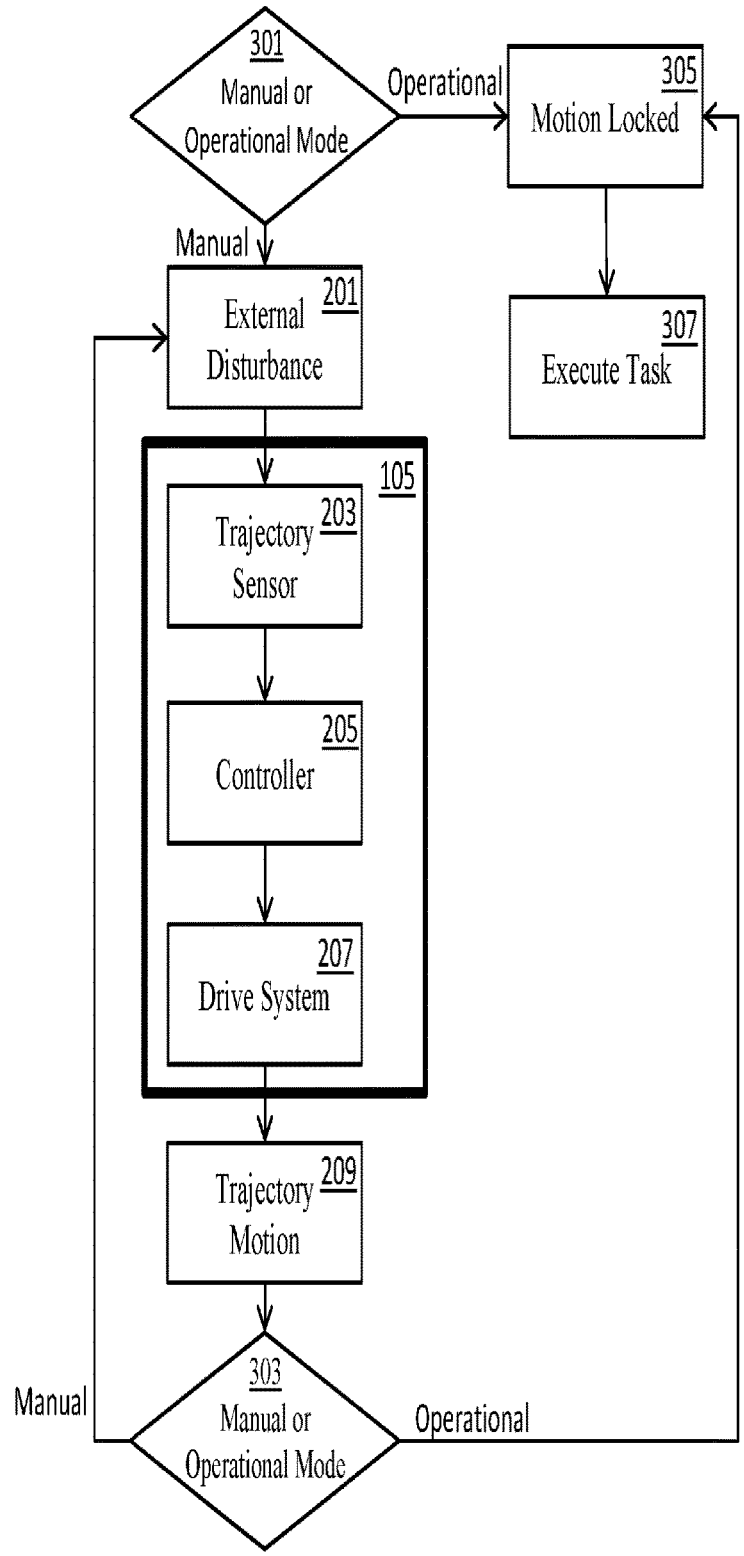
FIG. 3 is a flowchart of a method to control the trajectory of a robotics base with an operational mode and a manual mode in accordance with embodiments of the invention.

The robotics system 101 may also include a manual mode and an operational mode as shown in FIG. 3. With respect to FIG. 3, when the manual mode is active (Block 301), the user U is able to apply an external disturbance (Block 201) to the manipulator 105 and the base 103 moves accordingly (Blocks 203-209). When the operational mode is active, an external disturbance 201 applied to the manipulator 105 will not cause the base 103 to move. The base is fixed in place (305). The base 103 may be locked in place by applying a hydraulic or electric brake to the wheels, by deflating a bladder, or removing power to the drive system 207. The operational mode is active when the end-effector 107 needs to perform a specified task (307), for example, milling the femoral canal in total hip arthroplasty. The two modes provide a safety mechanism such that the robot 101 does not move when performing a task with the manipulator 105. The switching between the manual mode and the operational mode may be accomplished with an external mechanism incorporated with the robotics system 101 or an external device electrically or wirelessly connected to the robotics system 101 (Block 303). For example, a button may be located on the base 103, the manipulator 105, the monitor 109 with touch-screen capabilities, or any other region of the robotics system 101. Likewise, an external device such as a controller or joystick connected to the robotics system 101 may allow one or more users to activate or inactivate the manual or operational mode. In a particular inventive embodiment, the manual or operational mode may be activated/inactivated using visual or audible signals.

In specific inventive embodiments, the manual mode may only be active as the user U pushes and holds an input parameter illustratively including a button or touch sensitive surface or screen. For example, the input parameter may be located on the manipulator 105 near or on the end-effector 107, wherein the base only moves according to an external disturbance if the input parameter is activated (i.e., pushing and holding down a button). Once the input parameter is deactivated (i.e. removing pressure from the button) the base will then cease movement and remain stationary until the button is pressed again. In a particular embodiment, the input parameter may be entirely deactivated in operational mode such that even if a user or other object comes in contact with the input parameter, the base 103 remains stationary such that the manipulator task will not be interrupted or altered.

In specific inventive embodiments, when maneuvering the base 103, the various links 117 and joints 119 of the manipulator 105 may be static. In a particular embodiment, the various links 117 and joints 119 may be given a small range to rotate or linearly move based on the external disturbance. For example, when in manual mode, a revolute joint may be able to rotate 'x' degrees or a prismatic joint may be able to move linearly a distance 'y'. By allowing the joints 119 to move a small range based on the external disturbance, the linear, rotary, or spherical encoders may measure the corresponding direction and velocity. A program working with the controller may read all of the data from each of the joint encoders and calculate the desired direction to move the robotics base 103. Therefore, the encoders already incorporated with each of the joints 119 may be used as the sensors for the controller and drive system to move the base 103 in a desired direction and velocity.

Figure 4:
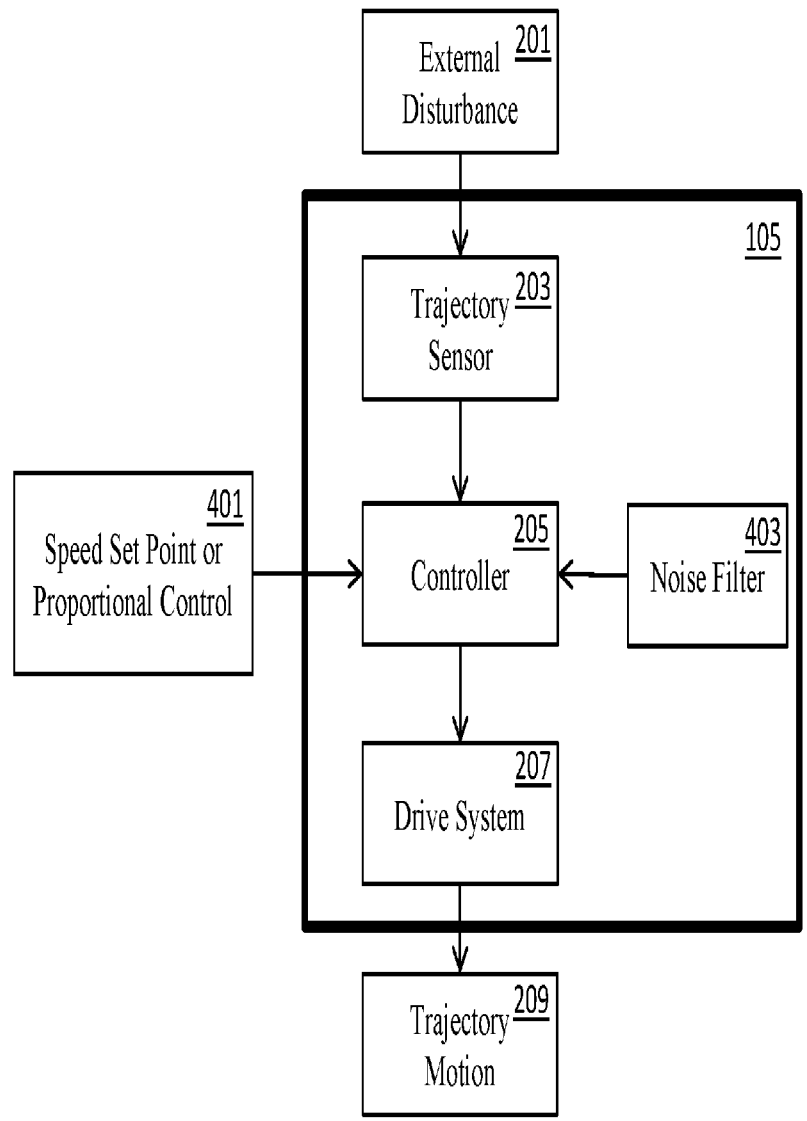
FIG. 4 is a flowchart of a method to control the trajectory of a robotics base with different velocity control modes in accordance with embodiments of the invention.

With respect to FIG. 4, the user U may specify to the robotics system 101 a speed set-point or proportional control (Block 401). For example, prior to applying an external disturbance 201 to the manipulator 105, the user may select a desired speed. If the robotics system 101 needs to travel a long distance with minimal impeding obstacles, the user U may select a high speed to move the base 103. If the robotics system 101 is approaching a patient and needs to be accurately positioned and oriented, a user U may select a low speed to move the base 103. The speed set point or proportional control 401 provides a high level of precise control that would otherwise be unobtainable using a conventional steering mechanism. Therefore, no matter how much force or pressure the user U applies to the manipulator 105, the controller 205 ensures the drive system 207 operates at only the set-point speed in the direction of the external disturbance 201. In specific inventive embodiments, the user U may select a proportional velocity control option. The controller 205 may be programmed to convert the magnitude of the pressure or force applied to the manipulator 105 to a proportional velocity. More pressure or force applied to the manipulator 105 corresponds to a higher velocity. A throttle or amplifier may control the voltage or power supplied to the drive system such that the velocity of the base 103 corresponds to the amount of force and/or torque applied on the manipulator 105. In a specific embodiment, the user U may choose between a set-point speed mode, a proportional velocity control mode, or a combination thereof. For example, the user U may define a range of speeds, or a maximum speed such that in proportional velocity control mode, the speed of the base 103 will not move above or below the desired range of speeds.

In specific inventive embodiments, the controller 205 is programmed with a noise filter (Block 403). The noise filter 403 ensures that only the desired external disturbances 201 applied by the user U are used to determine the correct trajectory. Therefore any vibrations created by the system 101 or from the external environment may be filtered, and the filtering resulting in smooth and accurate motions.

While the robotics system 101 is in manual mode, an emergency breaking system may be incorporated. For example, if a rapid torque or jerk is applied to the manipulator 105 above a specified threshold, the base 103 will not move and remain stationary. The controller 205 may receive and read the high torque or jerk above the limit and subsequently not send an input signal to the drive system 207. The emergency breaking system provides an additional safety mechanism to the users, patients, and robotics system 101 components. Additionally, other sensors illustratively including light detecting and radar (LiDAR), sonar, distance measurement sensors, and combinations thereof may be attached to or incorporated with the base 103 or manipulator 105 to provide additional safety during manual motion. Therefore, the base 103 may automatically stop if a collision with an obstacle is imminent.

The robotics system 101 may further include a manipulator hand-guide mode. In manipulator hand-guide mode, the force/torque sensors incorporated with the manipulator 105 are active. However, the base 103 remains stationary while the user U may adjust the various links 117 and/or joints 119 of the manipulator 105. The force/torque sensors and/or the linear, rotary, or spherical encoders detect a trajectory of an external disturbance 201 applied to the manipulator 105 and a controller 205 sends signals to one or more joints 119 to power the links 117 in a desired position and/or orientation. For example, the base 103 of the robotics system 101 may be located in an operable workspace, but the manipulator 105 needs to be adjusted to a starting position to perform a task. In manipulator hand-guide mode, the base 103 will not move, but the forces applied by the user U to the manipulator 105 will drive the joints 119 in the desired position and/or orientation. A speed control mode, or a proportional control mode may be likewise incorporated with the manipulator hand-guide mode. Similarly, a button or other input parameter may be incorporated with the robotics system 101 or an external device to switch between the different modes as described with manual and operational modes.

In specific inventive embodiments, there may be a scenario when the base 103 needs to be adjusted and/or moved but the end-effector 107 needs to remain in a specific position and/or orientation. For example, the end-effector 107 may need to remain in a specific operating location relative to a patient or workspace, but the base 103 may need to be adjusted to perform a subsequent task and/or reach a new operable workspace. The manipulator 105 would therefore compensate for the motion of the base 103. Depending on the degrees of freedom of the robotics system 101, the position and/or orientation of the links 117 and joints 119 of the manipulator 105 would automatically update such that position and/or orientation of the end-effector remains the same while the base 103 moves.

The robotics system 101 may further include an automatic mode where a set of instructions may be programmed or are pre-programmed such that the base 103 moves automatically in a specified trajectory or set of trajectories without any user U interaction. Programmable manipulator instructions may control the manipulator by at least one of active control, semi-active control, and haptic control. In specific inventive embodiments, if the robotics system 101 is in automatic mode, any external disturbance applied to the manipulator 105 by the user U will override the automatic mode such that all future movements are based on the external disturbances 201. In a particular inventive embodiment, the manual mode is a compliment to the automatic mode. For example, if the automatic control veers off course, or needs to be adjusted, the user U may apply an external disturbance 201 to the manipulator 105 to make the desired correction. Additionally, a user U may teach the robotics system 101 a set of movements in manual mode that may be stored and automatically repeated in automatic mode.

In automatic mode, the robotics system 101 may automatically move to different operating rooms, traversing large distances. Once the robotics system 101 reaches the operating room, the robotics system 101 may stop, where a user U may take control of the robot 101 in manual mode to position the robotics system 101 precisely at the operating site. The robotics system 101 may include a variety of external sensors to sense the environment illustratively including cameras, servoing cameras, accelerometers, gyroscopes, inertial measuring units, optical receivers, optical transmitters, light sensors, contact sensors, pressure sensors, proximity sensors, touch sensors, temperature sensors, and any combination thereof. In specific inventive embodiments, the robotics system 101 includes optical receivers to receive information via visible light communication from light emitting diodes (LED) emitting transmitters located in the environment. For example, LEDs are capable of transmitting data to optical receivers. Various LEDs may be positioned in a hospital or other setting to help guide the robotics surgical system 101 to a desired location. Additionally, other sensors illustratively including light detecting and radar (LiDAR), sonar, distance measurement sensors, and combinations thereof may be attached to or incorporated with the base 103 or manipulator 105 to provide additional safety during automatic motion. Therefore, the base 103 may automatically stop if a collision with an obstacle is imminent.

In a specific inventive embodiment, wherein the transportation mechanisms are wheels, there may be two modes of wheel operation. In one mode, both wheels may rotate at the same time and move in the desired direction, which provides a floating motion used specifically for fine tuning the position and/or orientation of the base of the robot. A second, driving mode may be implemented wherein only the front or rear set of wheels are steered, and suitable for long distance motion. A combination of both modes of wheel operation may also be implemented.

Other Intuitive Motion Control Mechanisms

In addition to controlling the trajectory of the robotics base 103 by an external disturbance 201 applied to the manipulator 105 by a user U, the base 103 may be maneuvered by a user U using other external cues. For example in an inventive embodiment, the robotics system 101 may include a CCD or CMOS camera. The user U may point or perform gestures that correlate to a specific trajectory. The robotics system programmed to read the users gestures and correspondingly drive the base in the desired trajectory. Similarly, the robotics system 101 may be equipped with a microphone or other audible receiver to implement voice recognition for voice based commands. The user U may speak a set of instructions wherein the robotics system 101 is programmed to read, decipher, and translate the audible cues into signal commands to the controller 205. Subsequently the robotics base 103 is powered in the desired trajectory.

In a particular inventive embodiment, the robotics system 101 may include one or more touch sensors located on the base 103, the links 117, or joints 119 of the manipulator 105, or the end-effector 107 of the manipulator 105. The one or more touch sensors may be used as the detection mechanism to define the trajectory a user desires to position and/or orient the base 103. For example, four touch sensors may be incorporated on the end-effector 107 that may correspond to a motion in a forward, backward, left, and right direction. The user U applies a desired pressure on the appropriate touch sensor and the controller 205 sends the corresponding signal to the drive system 207 to power the base 103 accordingly. In another exemplary embodiment, a small touch sensor or display is incorporated with and/or electrically or wirelesssly connected to the base 103 or the manipulator 105. The small touch sensor or display illustratively includes a smart phone or similar devices where the user U may swipe and/or hold a portion of the device to designate the desired direction of motion.

In a particular inventive embodiment, the robotics system 101 may include light detection and ranging (LiDAR) capabilities. A laser range finder, or a one, two, or three dimensional laser scanner may be incorporated with the robotics system 101. The robotics system 101 with LiDAR capabilities may detect a user U or a specific object and subsequently power the base 103 in the trajectory of the user U or the object. Therefore the robotics system 101 would essentially follow the user U or object without any user interaction on the manipulator 105 or the base 103.

In a particular inventive embodiment, the robotics system 101 may incorporate a sensor to read a specific pattern such as a bar code or QR code. The user U may hold the pattern in front of the sensor such that the robot base is powered in the direction of the pattern. There may be multiple patterns with additional trajectory information. For example, an object in the shape of a cube may have different patterns on each of the six faces. A user may hold one pattern to the sensor directing the base in a forward direction, and subsequently change to a new face with a new pattern specifying a clockwise or counterclockwise rotational motion.

In a particular inventive embodiment, a transmitter may transmit subsonic signals in the environment that may be in possession of a user U. The transmitter may be attached to or incorporated with a small hand-held device illustratively including a dongle, or a remote controller. The transmitter and hand-held device may or may not be electrically or wirelessly connected to the robotics system 101. A receiver incorporated or attached to the robotics system 101 may be capable of triangulating the source of the transmitted signals from the transmitter such the base 103 is powered in the trajectory of the transmitter. The small hand-held device may include various buttons for additional control of the robotics system 101. For example, one or more buttons on the small hand-held device may stop the base 103 from moving, change the mode of operation (i.e., operational, manual, automatic modes), reduce the set-point speed, or change to a very delicate mode of operation to pass through doors, approach a patient, and perform fine maneuvering.

It should be appreciated that the robotics system 101 with other intuitive control mechanisms may be combined with the other various embodiments described in the foregoing detailed description.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes may be made in the function and arrangement of elements without departing from the scope as set forth in the appended claims and the legal equivalents thereof.

The invention claimed is:

1. A robotic system comprising:
   a base adapted to be mobile on a floor at a first location;
   a manipulator attached to said base and configured to assist with a surgical procedure;
   at least one sensor associated with said manipulator, said at least one sensor detecting a trajectory of an external disturbance on said manipulator;
   a controller to convert the trajectory detected by said at least one sensor to an input signal; and
   a drive system that receives the input signal, and in response to the input signal powers said base to move the base and the manipulator from the first location to another location on the floor corresponding to the trajectory of the external disturbance.

2. The robotic system of claim 1 wherein said base further comprises a bottom with at least one of wheels, inflatable bladder, and a continuous track.

3. The robotic system of claim 1 wherein the at least one sensor is one of a linear encoder, rotary encoder, transducer, Hall effect sensor, force sensor, or torque sensor.

4. The robotic system of claim 1 further comprising a processor to receive a set of programmable trajectory instructions to power the base in a pre-defined trajectory.

5. The robotic system of claim 1 wherein the trajectory is at least one of a direction, rotation, velocity, or acceleration.

6. The robotic system of claim 1 wherein the drive system powers the base proportionally based on the magnitude of a force or a torque detected by the sensor from the external disturbance.

7. The robotic system of claim 1 further comprising a manual mode and an operational mode.

8. The robotic system of claim 7 wherein said drive system is in an active state in the manual mode and an inactive state in the operational mode.

9. The robotic system of claim 7 wherein the manual mode is activated by an input device located on at least one of the base, the manipulator, an external controller and a monitor.

10. The robotic system of claim 7 further comprising a set of programmable manipulator instructions to be executed by said manipulator in the operational mode.

11. A robotic system comprising:
    a base adapted to be mobile on a floor at a first location;
    a manipulator attached to said base and configured to assist with a surgical procedure;
    at least one sensor to detect an external cue from a user;
    a controller to convert the external cue detected by said sensor to an input signal; and
    a drive system that receives the input signal to power said base in a trajectory corresponding to the external cue from the first location to another location on the floor.

12. The robotic system of claim 11 wherein the at least one sensor is one of a linear encoder, rotary encoder, transducer, Hall effect sensor, force sensor, torque sensor, video receiver and audio receiver.

13. The robotic system of claim 11 wherein said base further comprises a bottom having at least one of wheels, inflatable bladder, and a continuous track.

14. The robotic system of claim 11 further comprising a processor to receive a set of programmable trajectory instructions to power said base in a pre-defined trajectory.

15. The robotic system of claim 11 wherein the trajectory is at least one of a direction, rotation, velocity, or acceleration.

16. The robotic system of claim 11 wherein the external cue is at least one of a user's touch, a visual cue and an audible cue.

17. The robotic system of claim 11 wherein said drive system powers said base proportionally to the external cue, where the external cue is at least one of a magnitude of force or a magnitude of torque detected by the sensor from the external cue.

18. The robotic system of claim 11 further comprising a manual mode and an operational mode.

19. A method for intuitive motion control of a robotic system comprising:
    applying an external disturbance to a manipulator of the robotic system, wherein said manipulator is attached to a mobile base and configured to assist with a surgical procedure;
    detecting a trajectory of the external disturbance; and
    powering a drive system to move the base of the robotic system in the detected trajectory of the external disturbance from a first location to another location on a floor.

* * * * *